United States Patent
Ferguson et al.

(10) Patent No.: US 8,236,231 B2
(45) Date of Patent: Aug. 7, 2012

(54) ULTRASONIC INJECTION MOLDING ON A WEB

(75) Inventors: Dennis E. Ferguson, Mahtomedi, MN (US); Satinder K. Nayar, Woodbury, MN (US); Peter T. Benson, North St. Paul, MN (US); Stanley Rendon, Eagan, MN (US); Donald L. Pochardt, Hastings, MN (US); James N. Dobbs, Woodbury, MN (US); Daniel H. Carlson, Arden Hills, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 373 days.

(21) Appl. No.: 12/600,557

(22) PCT Filed: Jun. 18, 2008

(86) PCT No.: PCT/US2008/067318
§ 371 (c)(1),
(2), (4) Date: Nov. 17, 2009

(87) PCT Pub. No.: WO2008/157592
PCT Pub. Date: Dec. 24, 2008

(65) Prior Publication Data
US 2010/0159197 A1    Jun. 24, 2010

Related U.S. Application Data

(60) Provisional application No. 60/945,224, filed on Jun. 20, 2007, provisional application No. 60/945,217, filed on Jun. 20, 2007.

(51) Int. Cl.
*B29C 45/73* (2006.01)

(52) U.S. Cl. ... 264/403; 264/443; 264/478; 264/328.16; 425/115; 425/174; 425/174.2; 425/174.8 R; 425/547

(58) Field of Classification Search .............. 264/403, 264/404, 478, 443, 328.16, 69–72; 425/115, 425/174–174.8 E, 547
See application file for complete search history.

(56) References Cited

U.S. PATENT DOCUMENTS
2,965,932 A    12/1960    Knowles
(Continued)

FOREIGN PATENT DOCUMENTS
DE    202 15 458    2/2003
(Continued)

OTHER PUBLICATIONS

Chen, S.C., et al., "Rapid Mold Surface Heating/Cooling Using Electromagnetic Induction Technology", *Proceedings of the 2005 IEEE International Conference on Mechatronics*, (Jul. 10-12, 2005) Taipei, Taiwan pp. 771-776.

(Continued)

*Primary Examiner* — Jill Heitbrink

(57) ABSTRACT

Injection molding, parts onto a carrier web (34) located between mold halves (18,20). Flow of polymer melt into the mold is assisted by application of ultrasonic energy to the mold cavity. After the molding operation, mold halves are separated, and the carrier web is advanced, or indexed, to a next position for another molding sequence. Molding apparatus comprises a moving mold face (20), that can move toward and away from a first mold member (18) (which can be stationary) in which the mold cavity is located, a means (24,25,26,30,32) for moving and/or indexing carrier web between the first mold member and the moving mold face, means (16) to inject polymer melt into the mold cavity, and an ultrasonic system (42) providing ultrasonic energy to the mold cavity. The carrier web can transport molded parts to subsequent process steps, such as coating, drying, inspection, curing, assembly or packaging.

17 Claims, 9 Drawing Sheets

U.S. PATENT DOCUMENTS

| | | | |
|---|---|---|---|
| 3,233,012 A | 2/1966 | Bodine, Jr. | |
| 4,489,033 A | 12/1984 | Uda et al. | |
| 4,515,543 A | 5/1985 | Hamner | |
| 4,793,954 A | 12/1988 | Lee et al. | |
| 4,848,630 A | 7/1989 | Niestrath et al. | |
| 4,921,671 A | 5/1990 | Staheli | |
| 5,017,311 A | 5/1991 | Furusawa et al. | |
| 5,376,317 A | 12/1994 | Maus et al. | |
| 5,470,300 A | 11/1995 | Terranova | |
| 5,851,474 A * | 12/1998 | Allan et al. | 264/403 |
| 6,318,248 B1 | 11/2001 | Capodieci | |
| 6,361,733 B1 | 3/2002 | Eicher et al. | |
| 6,464,485 B1 | 10/2002 | Iida et al. | |
| 6,629,831 B2 | 10/2003 | Wei et al. | |
| 6,846,445 B2 | 1/2005 | Kim | |
| 6,881,203 B2 | 4/2005 | Delmore et al. | |
| 7,132,632 B2 | 11/2006 | Huang | |
| 2002/0015748 A1 | 2/2002 | Miyajima et al. | |
| 2004/0173920 A1* | 9/2004 | Erickson et al. | 264/1.6 |
| 2005/0236729 A1 | 10/2005 | Arnott | |
| 2006/0249864 A1 | 11/2006 | Saito et al. | |
| 2007/0023941 A1 | 2/2007 | Duncan | |

FOREIGN PATENT DOCUMENTS

| | | |
|---|---|---|
| DE | 102 46 942 | 4/2004 |
| JP | 58 140222 | 8/1983 |
| JP | 11 138546 | 5/1999 |
| JP | 2004-034360 | 2/2004 |
| WO | WO 02/02180 | 1/2002 |
| WO | WO 2004/024415 | 3/2004 |
| WO | WO 2005/082596 | 9/2005 |
| WO | WO 2006/062974 | 6/2006 |
| WO | WO 2007/075614 | 7/2007 |
| WO | WO 2007/075806 | 7/2007 |
| WO | WO 2007/124393 | 11/2007 |

OTHER PUBLICATIONS

Chen, et al., "Rapid mold temperature variation for assisting the micro injection of high aspect ratio micro-feature parts using induction heating technology", *J. of Micromechanics and Microengineering*, (Jul. 2006) pp. 1783-1791, Institute of Physics Publishing.

Sato, A., et al., "Application of Ultrasonic Wave to Injection Molding", *Proceedings of the Polymer Processing Society 24$^{th}$ Annual Meeting*—PPS-24—Jun. 15-19, 2008 Salerno Italy.

International Appl. No. PCT/US2008/067318 International Search Report dated Nov. 3, 2008.

* cited by examiner

ULTRASONIC INJECTION MOLDING ON A WEB

CROSS REFERENCE TO RELATED APPLICATIONS

This application is a national stage filing under 35 U.S.C. 371 of PCT/US2008/067318, filed Jun. 18, 2008, which claims priority to U.S. Provisional Applications Nos. 60/945,217 and 60/945,224 both filed Jun. 20, 2007, the disclosures of which are incorporated by reference in their entirety herein.

TECHNICAL FIELD

The present disclosure relates to ultrasonic assisted molding methods and related devices.

BACKGROUND

Molded articles are well known and commonly used. Molded articles having delicate structures thereon can be challenging to mold and subsequently process and handle. Injection molding small delicate structures is typically accomplished by injecting molten material into a mold cavity and applying additional heat to the molten material while in the mold and allowing additional time for the molten material to flow into the small cavities in the mold.

A method of molding microneedles is disclosed in International Publication WO 2005/082596, and a method which may include the use of ultrasonic energy is disclosed in International Publication WO 2006/062974. A method of molding parts onto a continuous web of flexible material is taught in U.S. Pat. No. 4,921,671, and a method of making container caps on a thin sheet of plastic between upper and lower die parts which are brought together while an annulus of plastic is injected on said sheet is disclosed in U.S. Pat. No. 2,965,932. The use of electromagnetic induction to preheat molds is known.

DISCLOSURE OF INVENTION

The present disclosure provides methods of injection molding parts onto a carrier web. Some embodiments of the disclosed method include the application of ultrasonic vibrations to a carrier web, which is indexed between the mold halves. The disclosure also provides a method of processing and subsequently handling molded parts. Moreover, the disclosure provides a molded array of devices on a web and the machine for creating the molded devices.

The inventive method comprises:
providing an injection molding apparatus having a first mold member and a movable mold member that can move toward and away from the first mold member to close the mold, in which there is a mold cavity, in at least one of the first or movable mold members, having a plurality of microstructural features characterized by an aspect ratio of at least 2:1;
injecting a polymer melt into the mold cavity while it is closed;
applying ultrasonic vibrations to the mold cavity by means of an ultrasonic horn;
and applying at least one set of process parameters selected from:
A. positioning a carrier web so that, when the mold is closed, the carrier web is between the first mold member and the moving mold member, part of the web faces the mold cavity and part of it is outside of the closed mold;
B. heating the mold cavity by an electromagnetic induction heating means; and/or
C. heating the mold cavity by electric resistance heating.

Electromagnetic induction (EMI) heating can be used to apply rapid, localized heating of a microstructured tool within an injection mold cavity. EMI can be used to mold parts with sub-5 micrometer features that excellently replicate a mold pattern in a relatively short mold cycle time (e.g., less than 10 seconds) and with significant reduction in in-mold stresses and birefringence in the molded article produced, as compared with articles made without EMI.

"Microstructure" means microscopic features or structures (having at least one dimension (e.g., length, width or height) between 1 μm and 1 mm) on a larger article. Such features may be, for example cavities, grooves or projections (e.g., microneedles in a microneedle array on a disk of polymer (hereinafter called a land)).

Microneedles are small, tapered microstructures that arise from a base or land of an article (e.g., a disc or circular base of a microneedle array). The microneedles are elongated and tapered from base to tip and may have a shape like a pyramid, cone or those shapes disclosed in U.S. Patent Publication 2003/0045837 and PCT Publication WO 2007/075614, among others. Microneedles can pierce the stratum corneum of the skin to facilitate the transdermal delivery of therapeutic agents or the sampling of fluids through the skin. Height of a microneedle is normally less than 1000 μm, typically in the range of 20-500 μm, or 25-250 μm from the base to the tip, and the aspect ratio may be in the range of 2:1 to 6:1.

"Aspect ratio" means the ratio of height or length of a feature (such as a microstructural feature, like microneedles) to width or diameter at the widest part of such feature (such as the base of a microneedle where it intersects the land that serves as a base of a microneedle array). In the case of a pyramidal microneedle with a polygonal or rectangular base, the maximum base dimension used to find aspect ratio would be the diagonal line connecting opposed corners across the base.

An "array" means an arrangement of two or more articles or features on a surface in proximity to each other, which may or may not be in a particular geometric order.

"Percent fill" is the depth of a single microstructural feature that polymer melt is able to fill. For example, if a microneedle cavity is 250 μm deep and polymer fills it to a depth of 125 μm, percent fill would be 50%.

An apparatus used in the inventive method comprises:
An injection molding apparatus comprising:
 a first mold member;
 a moving mold member that can move toward and away from the first mold member;
 a mold cavity within the first mold member and facing the moving mold member;
 a web handling means for moving a web between the first mold member and the moving mold face so that part of the web faces the mold cavity and part of the web is outside of the area enclosed by the first and movable mold members when they are in the closed position;
 a means to inject melt into the mold cavity; and
 an ultrasonic system for providing ultrasonic vibrations to the melt in the mold cavity;
said apparatus further comprising at least one component selected from:
A. a web indexing means to index the carrier web to a different position along its length each time the moving mold member moves toward the first mold member to close the mold;

B. an electromagnetic induction heater capable of heating a mold insert within the mold cavity and/or metal surrounding the mold cavity; and C. an electrical resistance heating means.

A positioning means, capable of positioning the EMI heater close enough to the mold cavity to accomplish such heating if it is not already in such a position, can be used. So long as the EMI heater can be positioned close enough to effectively heat the mold cavity, other configurations can be used. For example, an EMI heater can be located within the first mold member in a position close to the mold cavity. In that case, a positioning means as described above would be unnecessary.

With reference to a mold, the term "feature" means a three dimensional cavity, recess, or depression within a mold cavity that may define, at least in part, the shape of an article to be molded, such as a microneedle or lens.

The filling of the very small features of a mold is aided by dynamic mold temperature cycling which controls the use of heat transfer means to adjust mold temperature. In dynamic mold temperature cycling, the mold is first heated to a temperature above the softening temperature of the polymer to be injected (e.g., above 149° C. for polycarbonate). High mold temperature helps to keep polymer melt viscosity low to facilitate filling the mold features and minimize viscoelastic skinning. After formation of the molded part, the mold is cooled below the softening point to help solidify the molten polymer. Methods of mold temperature thermal cycling are described in PCT Publication WO 2005/082596 and U.S. Pat. No. 5,376,317.

The efficacy of dynamic mold temperature cycling is limited by the rate of mold heating and cooling. Highly thermally conductive materials (e.g., beryllium-copper alloys) can be used to improve heat transfer, but the rate of heat transfer is limited by the properties of the heat transfer means used, such as oil.

The term "cycle time" means the time from closing of the injection molding apparatus, with the carrier web between the first and movable mold members, until the indexing of the carrier web, moving the molded article or articles away from the mold cavity area and positioning part of the carrier web for the next mold cycle. During each mold cycle, the cycle time should be sufficient to allow the mold cavity (including any micro-cavities in the insert) to be substantially filled with molten polymer and for the polymer to subsequently cool below the polymer softening point.

In the inventive method, filling mold features is also aided by use of ultrasonics and/or EMI heating of mold parts as part of the molding cycle. After the polymer melt has filled the mold cavity, the mold is cooled to a temperature below the polymer glass transition temperature to allow for ejection of the molded article from the cavity. The combination of process parameters in the inventive process enable shorter mold cycle times than are practical by practicing the prior art. The inventive process and apparatus enable injection molding microstructured articles (having features with dimensions of less than 5 μm) with good fidelity (i.e., good reproduction of the very small mold features) and mold cycle times of 20 seconds or less.

To maximize molded part density on a carrier web the inventive process can be configured to mold cavities in staggered positions on the carrier web. This concept, to be explained hereinafter, can yield an array of molded articles adhered to the carrier web in which the closest center-to-center, or edge-to-edge, distance between the molded articles is closer than the center-to-center, or edge-to-edge, distance between the mold cavities of the injection molding apparatus.

DETAILED DESCRIPTION

Figure 1:
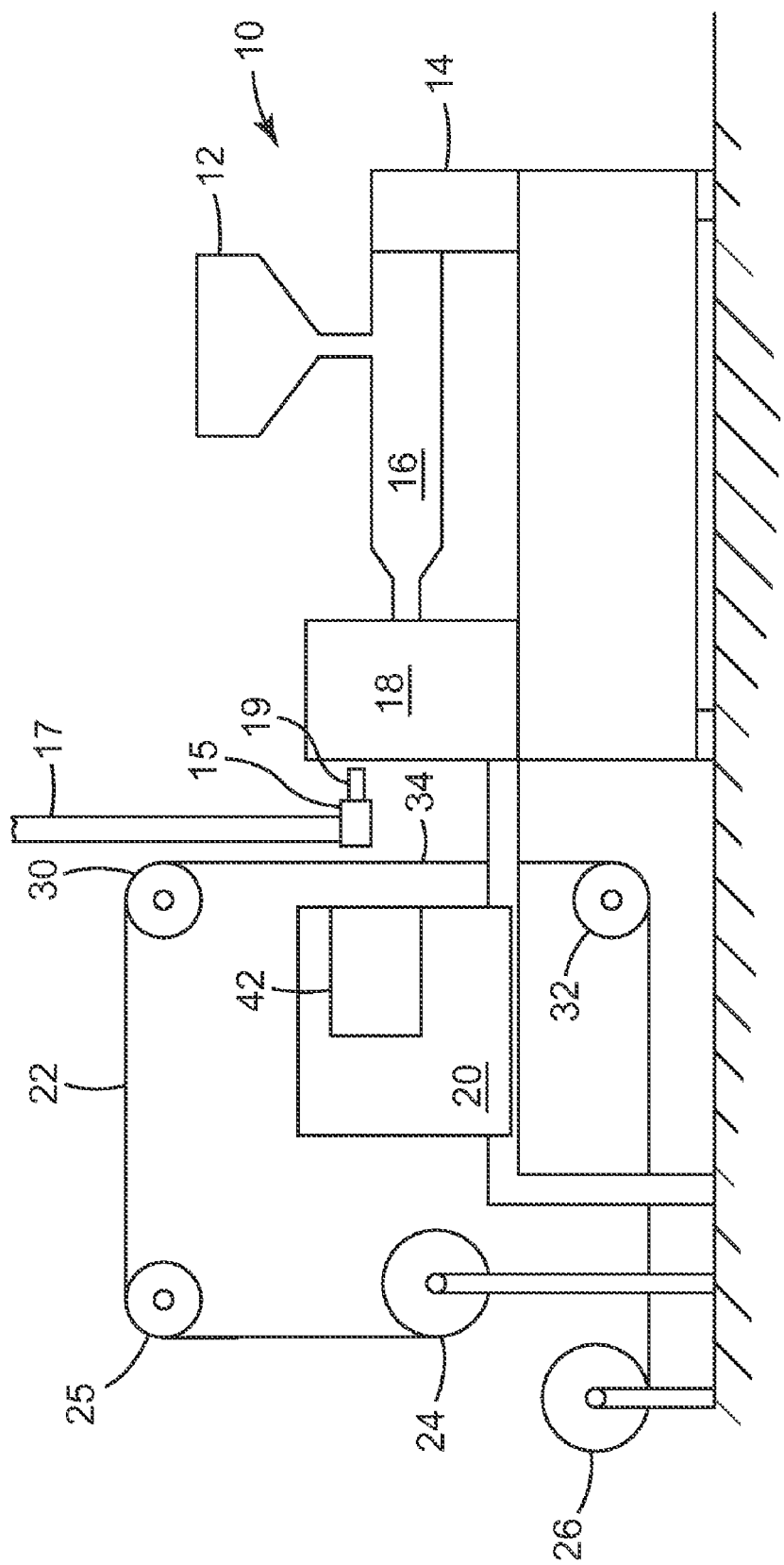
FIG. 1 is a schematic side view of a molding system according to the principles of the present disclosure.

Referring to FIG. 1, a schematic view of an injection molding system 10 according to an embodiment of the present disclosure is shown. In the depicted embodiment, the system 10 includes a hopper 12 for receiving the material to be melted (e.g., plastic or metal pellets encased in plastic), a motor 14 for powering the system, a heated chamber 16 for melting and feeding the material, a first mold member 18, and a second mold member 20 in which ultrasonic horn 42 is installed. In the depicted embodiment the first mold member 18 is stationary (although it could be movable) and the second mold member 20 moves towards and away from the first mold member 18.

The molding system 10 further includes a web indexing system 22. In the depicted embodiment the web indexing system includes a feed roll 24, an uptake roll 26, a pull roll 32, and a number of guide rollers 25 and 30 between the feed roll 24 and uptake roll 26. The indexing system 22 is configured to move a web 34 between the first mold half (first member) 18 and second mold side or movable mold member 20. The web 34 is referred to interchangeably herein as a film or carrier web. In describing location or movement with respect to the carrier web, location or movement in the direction in which the web is being moved along its length is called "down-web", and a location or movement in the opposite direction (toward the direction from which the web is being unwound) is called "up-web".

Though typical injection molding systems do not include a web indexing system, it should be noted that a system wherein a web is passed through a mold is described in PCT Publication No. WO 2007/075806 titled Manufacturing Microneedle Arrays, which is herein incorporated by reference in its entirety. It is within the skill of the art to design a web indexing system to index carrier web 34 between mold members 18 and 20. Web indexing systems are known in the art as exemplified by U.S. Pat. Nos. 4,848,630 and 5,470,300.

An electromagnetic induction heater 15 is shown between the first mold member 18 and web 34. EMI heaters are known, and this one has an induction coil housing 19 containing an electromagnetic induction coil. Induction heater 15 is attached to arm 17 that is attached to an actuator (not shown) to raise and lower the induction heater and position it close to first mold member 18. In one embodiment of the inventive molding process, the EMI heater is placed in close proximity to the mold cavity (e.g., >0-2 mm gap between the face of the mold plate 37 (see FIG. 2) and induction coil housing 19) to provide rapid, localized heating of the surfaces of the mold cavity and insert. Electromagnetic induction heating is used in conjunction with dynamic mold temperature cycling (discussed above). In the injection molding of articles with micro- or nano-features, the temperature of the surfaces to which the polymer melt is exposed can affect the quality of the molded article, and EMI heating combined with dynamic mold temperature cycling is used as a means to rapidly raise that surface temperature for each mold cycle.

EMI heating apparatus are available commercially from such companies as MSI Automation, Inc., Wichita, Kans., U.S.A. A typical EMI heater would have a power of 1-5 KW and provide output frequency in the range of 25-450 KHz for surface heating. In the development of this invention an EMI apparatus was used having the following characteristics: approximately a 2.54 cm. diameter, water cooled, copper induction coil surrounded by a ceramic housing, (about 3.18 cm diameter and 4.45 cm long) 1500 W power, actual power used being 700 to 1250 W (depending on the power setting which ranged from 1 to 10), 120 Volts, 13 Amps and 25 to 50 kHz of output frequency. A reasonable range of induction heating time is 6 to 12 seconds for the system described herein. The diameter of the circular mold cavities 33 (see FIG. 2) in the apparatus used in developing this invention was about 12.7 mm. The EMI apparatus used was larger in diameter than needed. Ideally, a smaller EMI heater would be used having a surface approximately congruent with the mold cavity or mold cavity cross section.

With the use of a 1500 W EMI heater, with induction power settings about 50% of maximum power capacity, a mold insert for microneedles reached temperatures between 121° and 177° C. which is useful for molding microneedles from polycarbonate. Because EMI heating is focused on the surface of the mold cavity or insert, rapid heat dissipation (e.g., into the mass of surrounding metal and heat transfer fluid) can occur after filling the mold cavity. In general, gaps between the electromagnetic induction coil housing and the mold plate face in the range of about 1.5 to 2 mm led to approximately similar temperature profiles (i.e., curve of insert temperature vs. induction coil power setting); whereas, at a smaller gap of 1016 μm, the resulting temperature increase in the mold insert was higher at comparable induction activation times (3-8 seconds).

Figure 2:
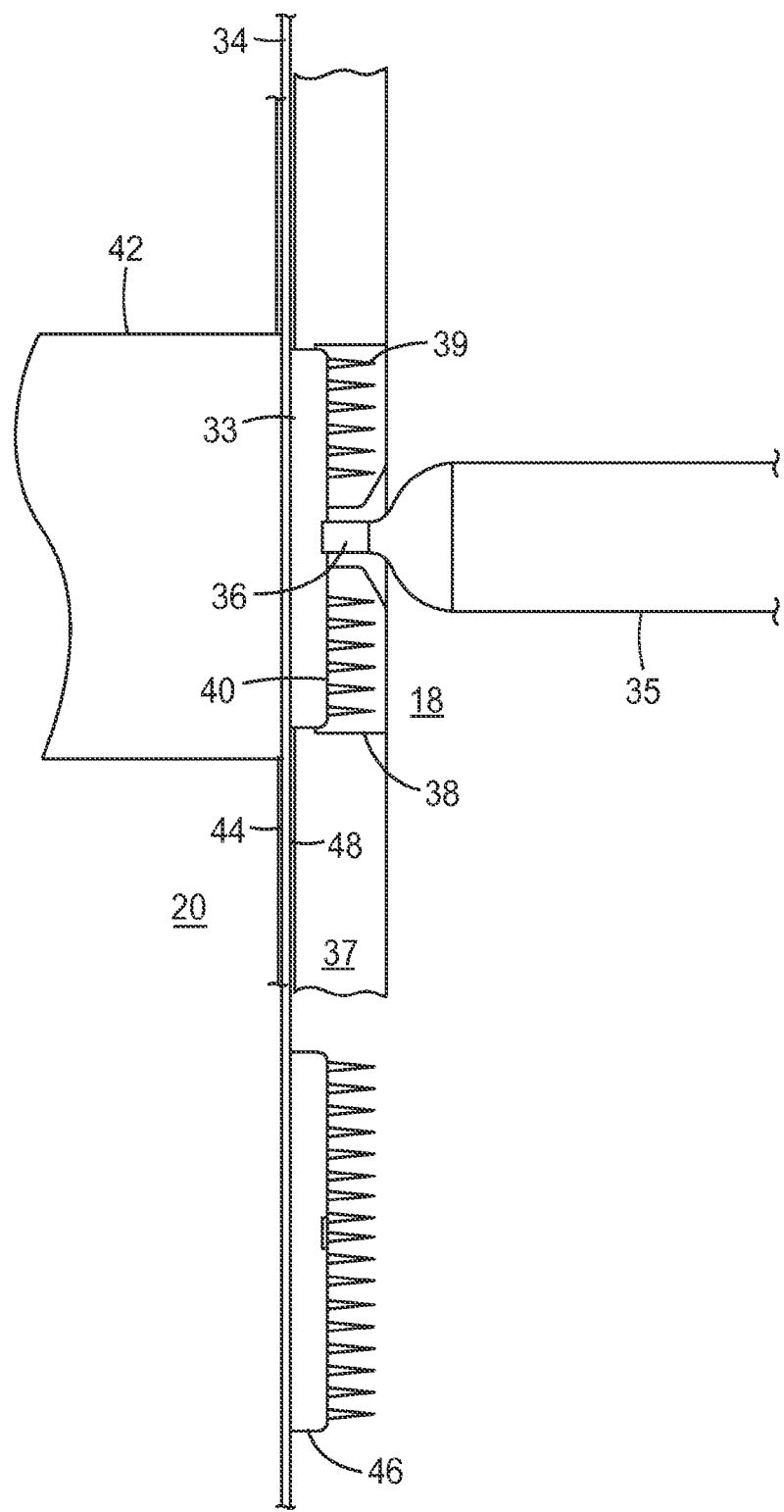
FIG. 2 is a schematic cut-away view of a mold cavity in a closed position showing articles molded on a first side of a carrier web.
Figure 3:
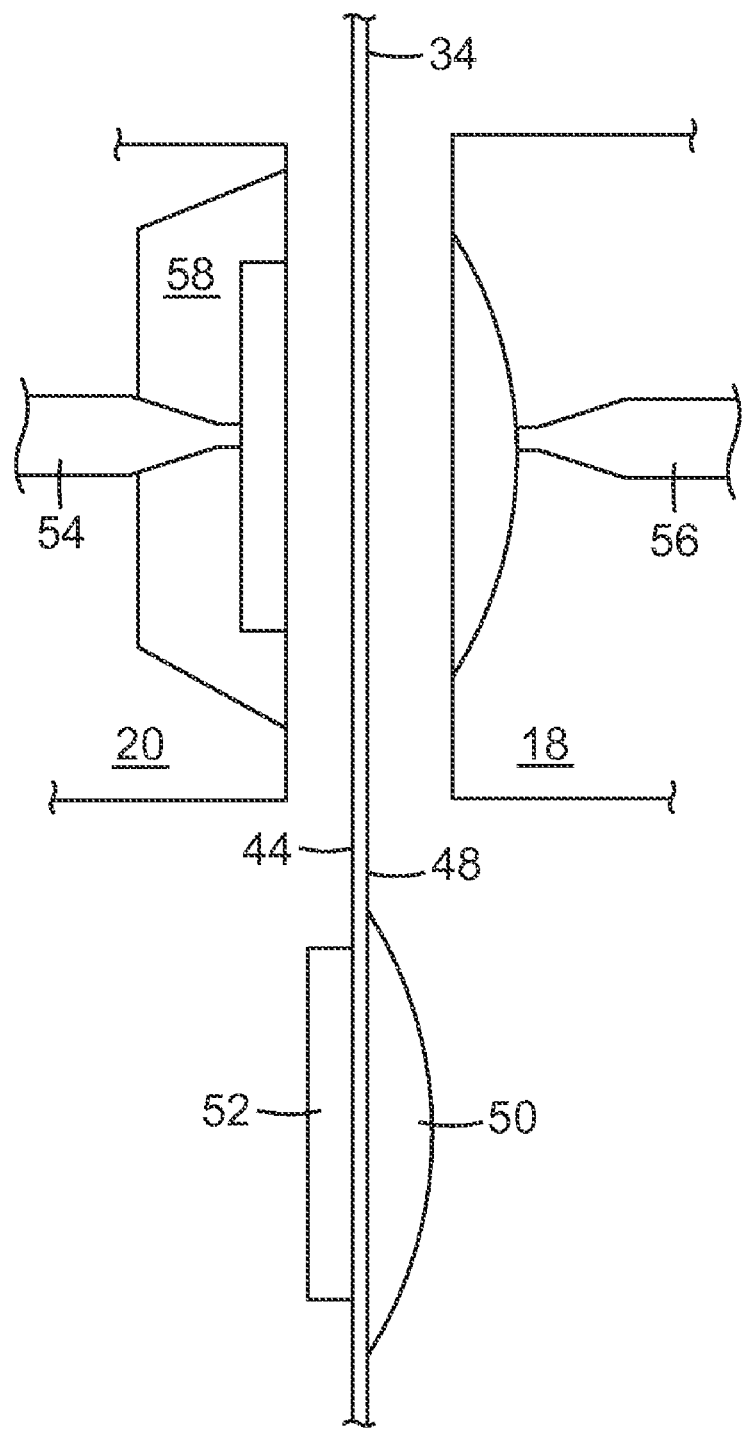
FIG. 3 is a schematic cross-sectional view of a mold cavity showing features molded on a first side and a second side of a carrier web.

Referring to FIGS. 2 and 3, cross-sectional views of embodiments of a mold cavity are shown and described in greater detail. FIG. 2 depicts an embodiment wherein the molded article 46 is located on only the first side 48 of a carrier web 34. FIG. 3 depicts an embodiment wherein the molded features 50, 52 are located on both the first side 48 and the second side 44 of the carrier web 34.

The polymer used in the injection molding process to make molded articles may comprise a variety of polymers selected based on properties such as ability to accurately reproduce the desired pattern of the mold cavity and insert, strength and toughness of the molded polymer, and compatibility of the molded polymer with the intended use. For example, one might choose a polymer or polymer blend or compound capable of forming relatively rigid and tough microneedles that resist bending or breaking in use. Some useful polymeric materials have: a melt-flow index greater than 5 g/10 min., 10 g/10 min., or 20 g/10 min. measured by ASTM D1238 at 300° C. and 1.2 kg. weight; a tensile elongation at break (measured by ASTM test D638 (2.0 in/min.)) greater than 100%; and impact strength (measured by ASTM D256, "Notched Izod" 23° C. greater than 5 ft-lb/inches. Some useful polymers are: polyphenyl sulfides, polycarbonates (e.g., Lexan HPS1R resin from Sabic Innovative Plastics, Pittsfield, Mass.), polypropylenes, acetals, acrylics, polyetherimides, polybutylene terephthalates, polyethylene terephthalates, and blends of such polymers.

The temperature of the metal surfaces of the mold cavity during filling and packing of the polymer melt into the cavity depends on the polymer used. Temperature is desirably sufficiently high to yield a low melt viscosity to improve the flow of polymer into microstructure cavities of the mold, but not high enough to degrade the polymer. Typical mold temperatures for molding polycarbonate are in the range of 60° C. to 200° C. or 120° C. to 175° C. during filling and packing, and in the range of 65° C. to 120° C. during ejection of a molded part from the mold. Temperature can be controlled by heat transfer means such as electric resistance heating near the mold cavity and/or heat transfer fluid (e.g., in a tube or tubes) in close proximity to the mold cavity (e.g., oil in a temperature range of 60°-150° C. or water in a temperature range of 27°-60° C.). One form of electric resistance heat comprises making electrical connection with the metal mold insert (e.g., insert 38 in FIG. 2) and using the insert itself as a resistance heater. In such an arrangement, a high current, low voltage transformer can be used so supply electricity to the resistance heater, e.g., about 40-150 amps and about 0.5-4 volts. The mold cavity may also be heated by other known means, such as: radiant energy, e.g., infrared energy or laser; or hot air flow from a heat gun.

Referring particularly to FIG. 2, the carrier web 34 is shown between first mold member 18 and a movable mold member 20. The carrier web 34 in the depicted embodiment is constructed of a polycarbonate film, however, it should be appreciated that the web 34 can be constructed of many other different materials (eg., metal foil, porous or non-porous polymer, woven, non-woven or knitted cloth composite, etc.). For carrier webs in this process, the term "composite" means a web comprising more than one raw material, such as a web made of both metal and polymer or laminates of metal and polymer film, cloth and polymer, or paper and polymer. Examples of suitable polymers for the carrier web are: polypropylenes, polycarbonates, polyethylenes, polyimides and polyesters. Carrier web thickness may be in the range of 5 to 1250 μm, or between 25 and 500 μm, and is preferably less than 250 μm.

By using a carrier web, the use of sprues and/or runners (common in injection molding, but wasteful of expensive polymer) can be minimized or eliminated. The carrier web eliminates the need for a cold runner for handling molded parts after ejection from a mold. The carrier web between the movable and first mold members can also serve as an insulator, resisting heat transfer from the mold cavity, helping retain heat which has the effect of keeping the polymer melt at a lower viscosity for a longer time.

In the depicted embodiment the first mold member 18 includes an injection gate 36, connected to a hot manifold nozzle 35, which directs molten material directly into the mold cavity 33. Although gate 36 is in the center of cavity 33 which is circular, there could be other locations for the injection gate, and locating the gate (or gates) is within the skill of the art. In the depicted embodiment the mold cavity 33 is within mold plate 37 which is attached to first member 18. The hot manifold nozzle 35 functions via the retraction of a pin which opens the exit of the nozzle and releases the polymer melt into the mold cavity. The insert 38 includes a cavity-facing surface 40 that includes micro-cavities 39 therein (e.g., cavities used to form microneedles). While it is inside the mold cavity, the insert is considered part of the cavity. A mold insert (sometimes called a stamper) used to make injection molded microneedles (or other articles having microstructure) can comprise a nickel tool electroformed in the shape of a negative of a microneedle array (see WO 2005/082596, pages 6 and 9). The mold configuration with insert 38 enables the same mold cavity 33 to be used to mold a number of different articles 46 by exchanging the mold insert 38 for one of a different shape or with different details.

In the inventive process, the mold cavity 33 is closed by moving the movable mold member 20 into contact with carrier web 34, clamping the mold with sufficient force provided by the injection molding machine. Then, polymer melt is injected into the mold cavity, and pressure may be used, in part, to fill the mold cavity with the melt. Part of the injection of polymer melt into the mold cavity may be based on reaching a certain pressure within the mold cavity ("pack pressure"). Pack pressure (e.g., in the range of 3.5 to 414 mega-Pascals (MPa) or 34.5 to 138 MPa) is applied for a finite time (referred to as "hold time"). A pressure above 103 MPa may be used to achieve uniform filling of the mold micro-cavities. Pack pressure is released, and the material within the mold cavity is cooled to an ejection temperature normally at or below the polymer softening temperature. Then, the mold members are separated, and the molded article is ejected from the mold cavity.

Useful parameters for the inventive process are: injection velocity of 60-360 mm/sec; pack pressure of 3.5-207 MPa, preferably 103-138 MPa; hold time of 0.5-10 seconds; mold temperature at injection (for polycarbonate) of 49°-150° C., preferably less than 121° C.; mold temperature at ejection (for polycarbonate) of 49°-138° C., preferably less than 121° C.

In the depicted embodiment, the movable mold member 20 of the injection molding apparatus includes a mechanism for applying auxiliary energy to the molten material while the molten material is inside the mold cavity. In the depicted embodiment the mechanism is an ultrasonic horn 42, which is configured to produce ultrasonic vibration energy. The ultrasonic horn used in developing this invention was solid, but it may be hollow. Materials of construction for the horn are within the skill of the art, but are typically titanium, aluminum or steel. The horn used in developing this invention was titanium.

In the depicted configurations, carrier web 34 is pressed against the horn 42 which directs ultrasonic vibration to the second side 44 of the web 34. The ultrasonic vibrations are transmitted through the web 34 to the molten material within the mold cavity. Ultrasonic vibrations may be used during the velocity-pressure switchover in the injection molding process (period when the injection molding machine is switching from filling the mold cavity with polymer melt to building pressure within the cavity).

Frequency of the energy can be in the range of 5,000-60,000 Hz, possibly 10,000-60,000 Hz, more typically 20,000 Hz-60,000 Hz, or 20,000-40,000 Hz. For a 20,000 Hz frequency, the peak-to-peak vibrational amplitude of horn 42 is typically less than 127 μm and can be less than 51 μm. Amplitude is a function of horn shape and excitation input. Amplitude in the range of 7.5 and 15 μm has been found useful. The ultrasonic energy is generally supplied by using a power source (e.g., in the range of 500 to 5000 Watts) to supply electrical energy of the desired frequency. Electrical energy is fed to a converter or transducer that transforms it into vibrations which can be amplified or boosted and transmitted via the horn.

The energy imparted to the molten material causes the material to further flow within the mold cavity. The horn transfers energy to the polymer melt so that it flows more readily into the micro-cavities of the mold insert. Locating the injection gate 36 in the center of the cavity has the advantage of reducing the wattage or energy required in applying ultrasonic vibrations, as compared to other gate locations (e.g., at the perimeter of the cavity). This allows the potential for more mold cavities to use the ultrasonic energy supplied by a single power supply (e.g., 5000 W).

The attachment of molded articles to the carrier web is affected by the amplitude of the ultrasonic vibrations. For example, when using polycarbonate film and polycarbonate melt material, peak-to-peak amplitude of 2.5-7.5 μm provides a weak bond between molded articles and the carrier web; while also giving a percent fill below 50%. Amplitudes between 7.5 and 15 μm yield good bond strength between the molded article and the carrier web along with improved percent fill (e.g., >75%). Amplitudes above 15 μm give excellent bond strength and enhanced percent fill (e.g., >85%). After the molded articles 46 on the carrier web 34 are formed, that portion of web 34 carrying the molded articles is indexed out of the mold and a new portion of the web 34 is indexed into position facing the mold cavity.

Referring particularly to FIG. 3, molded features 50, 52 are depicted on both the first side 48 and the second side 44 of the carrier web 34. The depicted embodiment includes injection gates 56, 54 on each of the first mold member 18 and movable mold member 20, and a horn 58 is included on the movable side 20. It should be appreciated that many alternative gate and horn configurations are possible. In the depicted embodiment the mold feature 50 has a domed cross-sectional shape and the mold feature 52 has a rectangular cross-sectional shaped. Moreover, the features 50, 52 are opposite each other and cooperatively form a useful device (e.g., an optical lens). It should be appreciated that in alternative embodiments the features 50, 52 on either side of the carrier web 34 can be the same or different in shape and/or material. It should also be appreciated, that in alternative embodiments the features 50, 52 do not need to be opposite each other on the carrier web 34.

In an alternative embodiment the carrier web can include perforations or one or more slits or holes therein that enable the melt to flow from one side of the web to the other side of the web. The carrier web may also have surface grooves or texture sufficient to allow venting of the mold. One may use sufficient injection pressure to inject polymer melt through the carrier web into a cavity on the opposite side of the web from the gate. According to such embodiments, mold features can be formed on both sides of the web with injection gates being on a single side of the web. It should also be appreciated that in alternative embodiments the gates 56, 54, can feed molten material into the mold cavity from many other directions (e.g., top, bottom, and sides).

Some lenses include features of low aspect ratio on one side and relatively high aspect ratio on the other. With a carrier web between the first and movable mold members, the low aspect ratio side of a lens may be embossed on the side of the web facing the movable mold member by a coining stroke. On the other side of the web, polymer melt is injected into the mold cavity, and the same coining stroke may simultaneously form the shallow or low aspect ratio part of the lens and high aspect ratio side of the lens under compression. By using the carrier web as part of the lens, the lens can be transported to a next manufacturing operation attached to the carrier web. This reduces handling and damage to the lens such as scratches and facilitates assembly. The compression or coining stroke allows thin lenses to be molded. Ultrasonic vibrations utilized during the mold cycle can increase the sharpness of detail, decrease the stress within a molded article, and allow thinner lenses to be molded.

Figure 4:
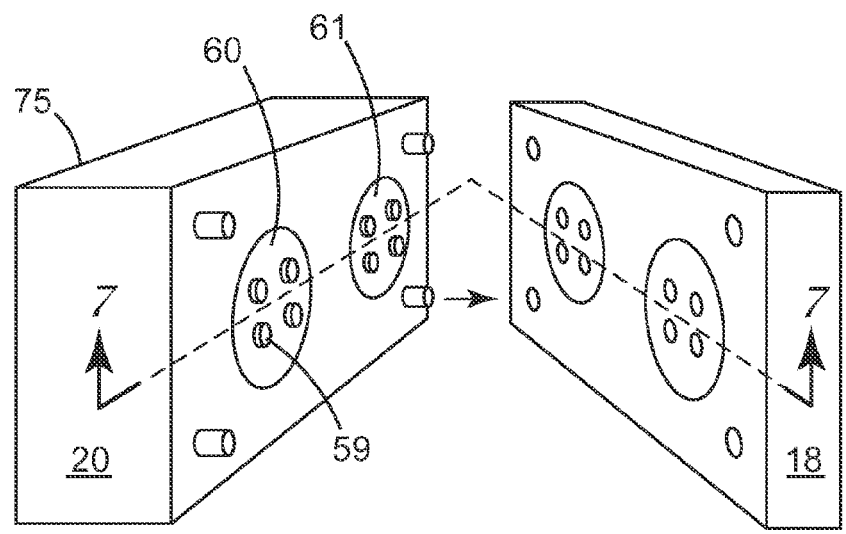
FIG. 4 is a schematic perspective view of a first mold side and a second mold side.

Referring to FIG. 4, the first and movable mold members 18, 20 are shown in a perspective view. The depicted embodiment illustrates that a plurality of separate molded articles can be simultaneously molded onto a carrier web. There can be 4, 8 or even 32 or more cavities in an injection mold, and it is advantageous to mold as many articles in a single mold cycle as possible. In the depicted embodiment the mold sides 18, 20 are configured to simultaneously mold eight separate articles onto a carrier web 34. In some embodiments the articles can be identical, whereas in other embodiments they can be different. The depicted embodiment further illustrates that the faces of ultrasonic horns 60, 61 can surround a plurality of mold features. In the depicted embodiment two circular-faced ultrasonic horns are located on the movable mold member 20. It should be appreciated that in alternative embodiments ultrasonic horns could be located on one or both of the mold sides.

Figure 5:
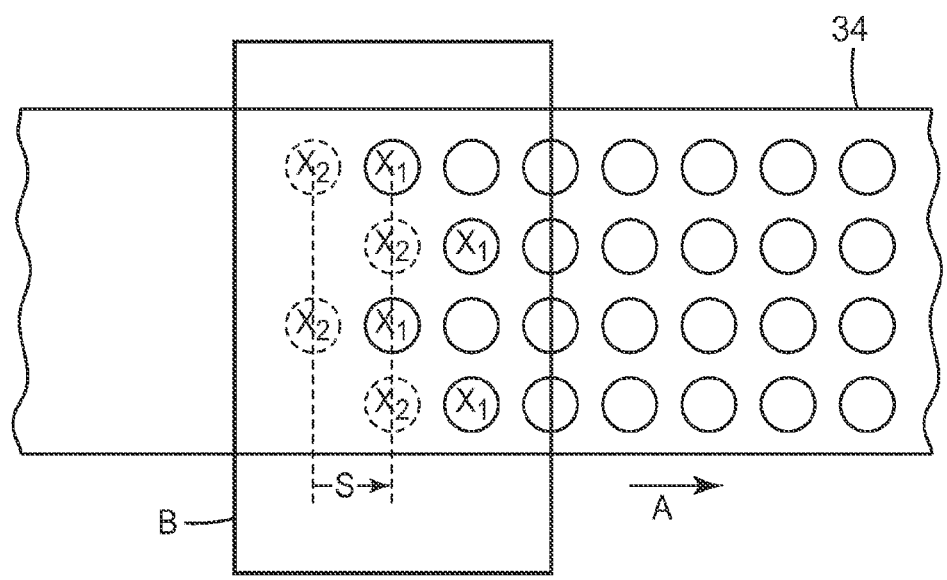
FIG. 5 is a top view of a plurality of articles on a carrier medium.
Figure 13:
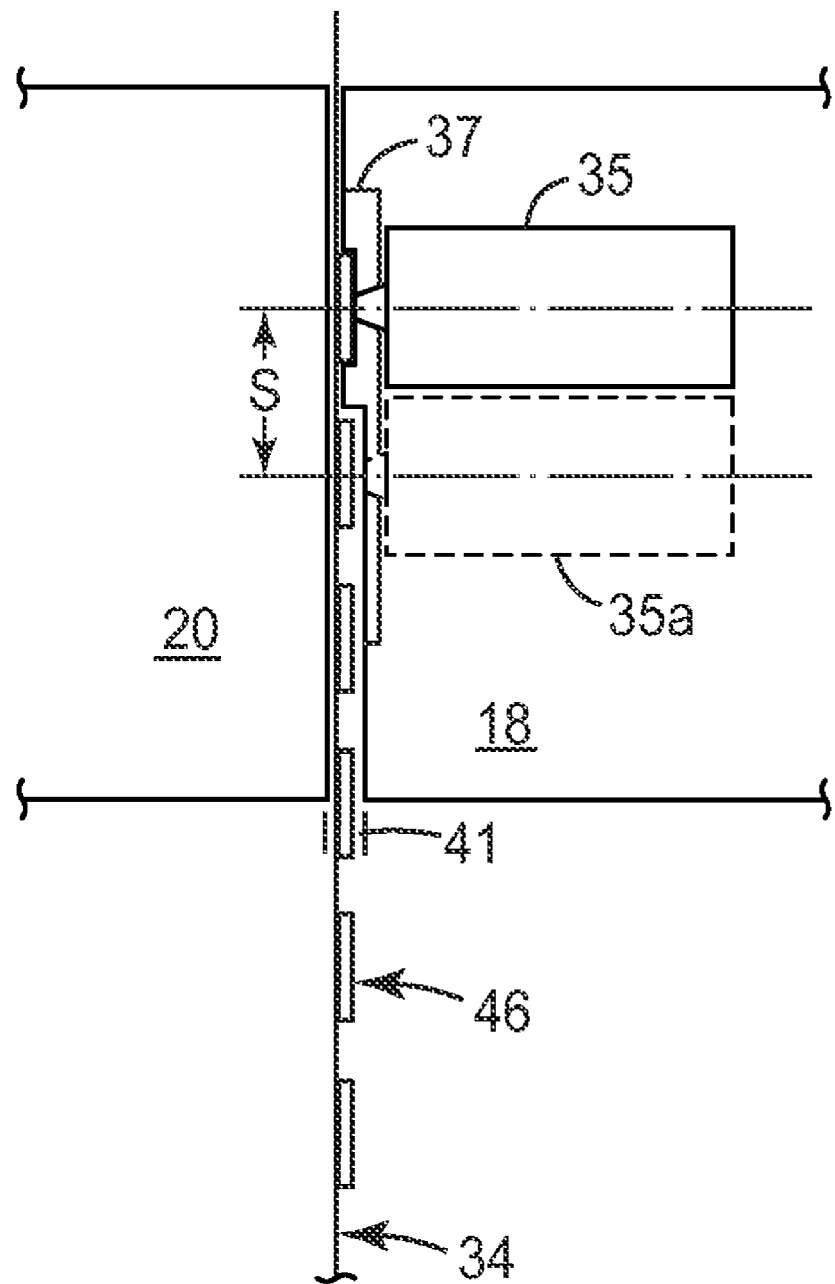
FIG. 13 is a schematic view of an injection molding apparatus nozzle arrangement to obtain the arrangement of molded articles on a carrier medium in FIG. 5.

Referring to FIGS. 5 and 13, a web carrier 34 is shown with a plurality of molded articles $X_1$ and $X_2$ thereon. The carrier web 34 serves as a support structure that allows the articles $X_1$ and $X_2$ to be handled as a group without actually picking and placing the articles separately. The carrier web 34 also serves the function of keeping the articles $X_1$ and $X_2$ oriented with respect to each other. In some embodiments runners between the articles $X_1$ and $X_2$ are used to maintain the orientation of the articles once they leave the mold. In the depicted embodiment the shortest or lateral distance between the articles $X_1$ and $X_2$ is about half the diagonal distance between adjacent mold cavities on the mold members. This is accomplished by molding articles $X_1$ and $X_2$ in two separate steps. For example, articles $X_1$ can be molded on the web carrier 34 in a first molding cycle, and then the web carrier with articles $X_1$ thereon can be indexed through the mold to a new position to mold articles $X_2$ onto the web carrier 34. In FIG. 5, arrow A shows the direction of carrier web movement, outline B shows the approximate perimeter of the first mold member 18, and S is the distance by which the carrier web is indexed from the mold cycle for articles $X_1$ to the next position for the mold cycle for articles $X_2$.

In FIG. 13, 35a represents the location of a manifold nozzle like manifold nozzle 35, but to inject polymer melt into a mold cavity in the next adjacent row of molded articles as shown in FIG. 5. Clearance cavities, such as cavity or offset 41 shown in FIG. 13, can be designed into the mold plate and first mold member to permit close positioning or nesting of molded articles and more efficient use of the web carrier. It should be appreciated that many other types of arrangements on the web carrier 34 are also possible. The same principle can be used in molding on both sides of the carrier web by designing movable mold member 20 with an offset to accommodate molded features on the side of the carrier web facing movable mold member 20.

The staggered or offset position of parts $X_2$ being molded at the same time shown in FIG. 5 allows room for the necessary components to support each mold cavity (such as the gate, manifold nozzle and heat transfer means such as tubes through which water or oil flow). Experience in the development of this invention indicates that a minimum spacing between molded articles on a carrier web could be as small as 5 mm.

Figure 6:
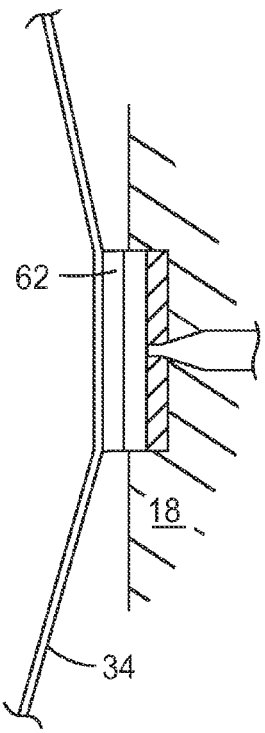
FIG. 6 is a side view of a part being pulled from the mold cavity of FIG. 2.

Referring to FIG. 6, a side view of a molded article 62 is shown being removed from the first mold member 18. In the depicted embodiment tension is applied to the web in a direction away from the first mold member 18 to pull the molded article 62 out of the mold cavity. It should be appreciated that ultrasonic vibrations may be used together with the tension to facilitate the release of the molded article 62 from the mold cavity. Although the carrier web enables removal of a molded article from the mold by means of the tension in the web alone, without using mechanical ejector means such as ejector pins, lifters or a stripper plate, in alternative embodiments pins or lifters may also be used in conjunction with or in place of the ultrasonic vibration and tension in the carrier web 34 to remove the molded articles 62 from the mold side 18. In a further embodiment, air pressure or vacuum assisted forces may be used in conjunction with or in place of the ultrasonic vibrations or tension in the carrier web 34 to remove the molded articles 62 from the first mold member 18.

Figure 7:
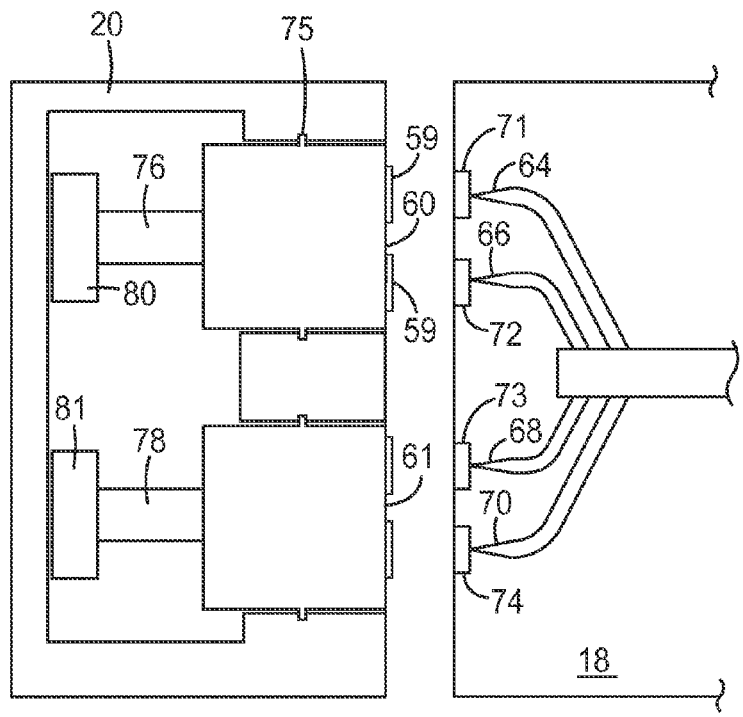
FIG. 7 is a schematic cross sectional view of the mold sides of FIG. 4.

Referring to FIG. 7, cross-sectional views of the mold sides of FIG. 4 are shown. The first mold side 18 is a stationary side with hot manifold drops 64, 66, 68, 70 directed to each of the mold cavities 71, 72, 73, and 74. The second mold side 20 is configured to move towards and away from the first mold side 18. In the depicted embodiment the movable mold member 20 includes an ultrasonic system for providing ultrasonic vibrations to the melt. The ultrasonic system includes horns 60, 61 that are connected to boosters 76, 78 which are connected to converters 80, 81. Ultrasonic horns 60 and 61 are oriented axially (ultrasonic vibration is in the same axial direction as the input excitation, i.e., vibrating along the axis of the horn). The horns have raised pads 59 (e.g., larger in diameter than the mold cavities and raised about 250 µm above the circular surface of the horn) on the side facing the mold cavities, and the horns are approximately aligned with and larger in diameter than a circle surrounding the mold cavities. The horns are mounted within movable member 20 by clamping at nodal flanges or rings 75, leaving clearance between the horns and the surrounding parts of the movable member.

It should be appreciated that the illustrated configuration is an example configuration. Alternative configurations can include different internal components or a different layout of the similar components or a different ultrasonic vibration direction. The horn may be oriented in a radial mode, for example. Although the ultrasonic horns in the drawings are illustrated on the same side as the movable mold member, the horn or horns could be located on the same side as the first mold member or in another location; so long as the horn is located and oriented in a position effective to direct ultrasonic vibrations into the polymer melt in the mold cavity.

Figure 8:
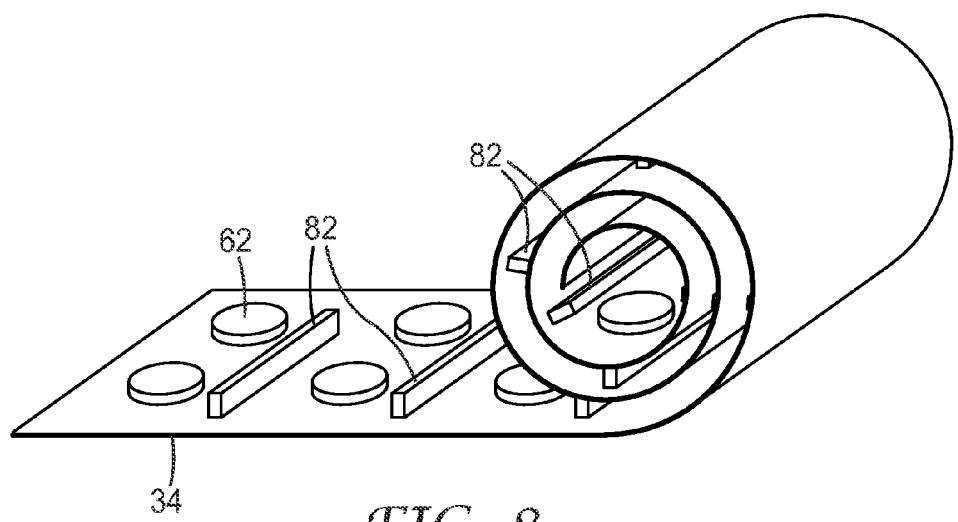
FIG. 8 illustrates partially rolled up carrier web having a plurality of molded articles thereon.
Figure 9:
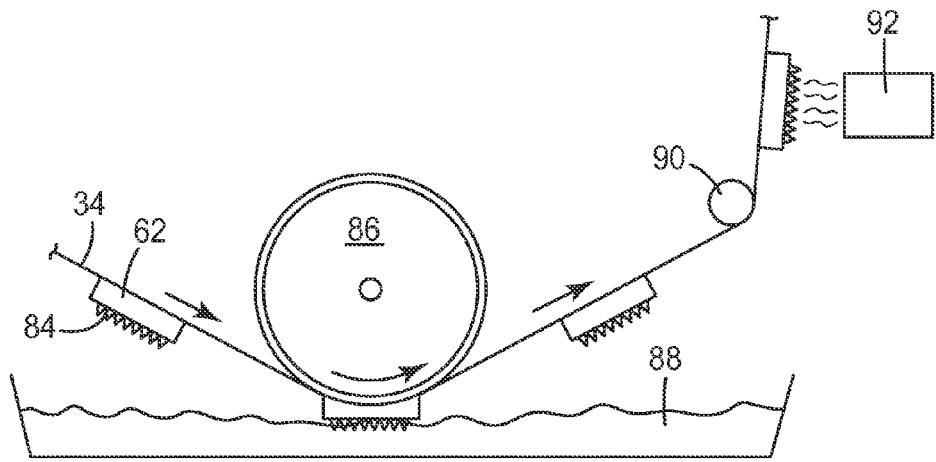
FIG. 9 depicts parts on a carrier web being further processed.

Referring to FIGS. 8 and 9, a method of handling and processing molded articles is shown. In particular, FIG. 8 depicts a method of packing molded articles by rolling the carrier web 34 onto itself. In the depicted embodiment spacers 82 are used to protect the molded articles from damage that might result from contact with the web carrier 34. In the depicted embodiment the spacers 82 themselves can be molded onto the carrier web. In an alternative configuration, the carrier web may be thermoformed in the molding process to provide spacers 82. It should be appreciated that alternative embodiments may not include spacers, as the molded articles may be configured such that contact with the carrier web 34 is unlikely to cause damage to the molded articles. It should also be appreciated that the carrier web 34 need not be rolled onto itself for packing and shipping. In alternative embodiments the carrier web 34 can be cut into sections and stacked one on top of the other for packing, shipping, processing, and handling purposes. In other alternative embodiments the carrier web 34 can be fan folded onto itself for packing, shipping, processing, and handling purposes.

FIG. 9 depicts the carrier web 34 with molded articles 84 thereon in processing steps subsequent to the molding process. In the depicted embodiment the carrier medium 34 provides a structure upon which the mold features 84 on molded articles 62 are formed. It also provides a means for handling the molded features 84 in a coating or a drying process. For example, molded articles can be coated by passing them over a roller 86 positioned above a tank of coating liquid 88. The molded articles can by dried by passing them over a roller 90, which directs the carrier web 34 past a drying device 92. The molded articles can also be inspected or sterilized while on the carrier medium.

Figure 10:
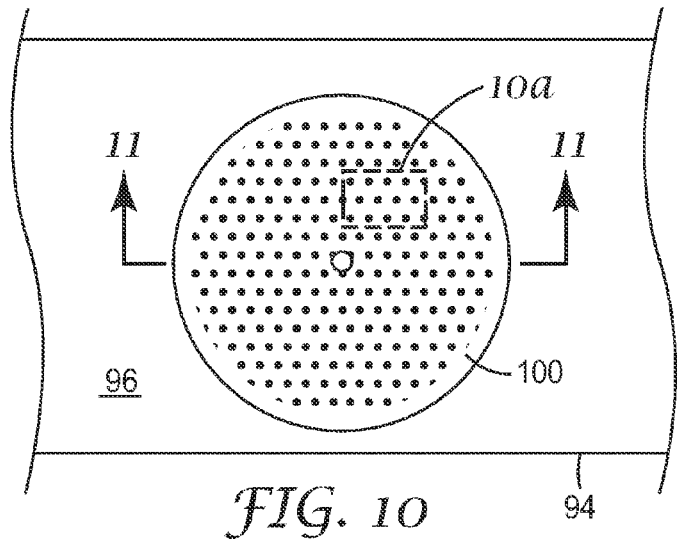
FIG. 10 is a top view of a microneedle array on a carrier web.
Figure 10A:
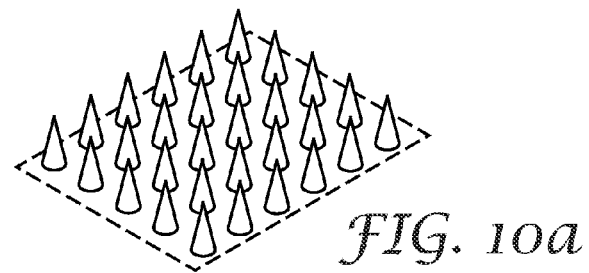
FIG. 10a is a detail showing microneedles of the microneedle array.
Figure 11:
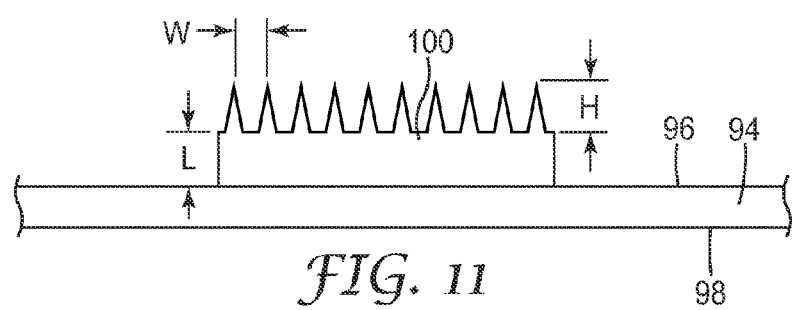
FIG. 11 is a cross-sectional view of the microneedle array of FIG. 10.

Referring to FIGS. 10 and 11, a molded article is shown and described in greater detail. The depicted embodiment includes a sheet 94 having a top surface 96 and a bottom surface 98. A molded article 100 is shown fused to the upper surface 96 of the sheet 94. In the depicted embodiment the sheet 94 is a flexible polymeric sheet (e.g., polycarbonate) that is melted to the article 100 (e.g., the sheet and the article can be ultrasonically welded together). A single article 100 is shown, but it should be appreciated that a plurality of such articles 100 can be spaced apart on the sheet 94. In the depicted embodiment the molded articles 100 include an array of microstructures thereon. In particular, the molded article 100 includes an array of microneedles thereon. In the depicted embodiment the height H of the needles is between about 25 to 5000 microns and the distance W from peak to peak (also called pitch) is between about 25 to 5000 microns.

The lower part of the article that serves as the base from which the microneedles rise is called the land, and distance L is the thickness of the land. Land thickness is determined by the dimensional relationship between the mold insert (having the microstructure defining the microneedles) and the depth of the mold cavity. The inventive process enables the manufacture of articles with a very thin land (e.g., L of about 250 µm or less). Lands about 50 µm thick, which can be made by this method, can enable an array of microneedles that has good conformability to the skin. It should be appreciated that numerous other articles are also possible, including articles that do not include microstructures thereon.

Figure 12:
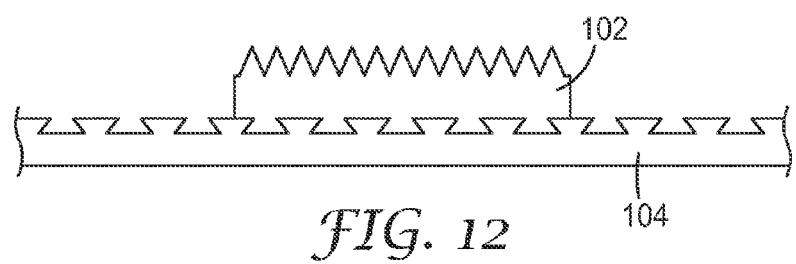
FIG. 12 is a cross-sectional view of an alternative embodiment of microneedle array of FIG. 11.

Referring to FIG. 12, an alternative embodiment of the articles of FIGS. 10 and 11 is shown. In the depicted embodiment the molded devices 102 are not fused with the sheet 104. In the depicted embodiment the molded device 102 and the sheet 104 are constructed of different materials and are connected in an interlocking manner. For example, the molded device 102 can include a polymeric or metal construction and the sheet 104 may include a paper construction or metal construction (e.g, metal foil). The devices 102 are melted onto the sheet 104 such that they interlock. The devices 102 could in alternative embodiments interlock with each other (e.g., in-mold assemblies are possible). In the depicted embodiment the sheet includes undercut features, but it should be appreciated that alternate configurations are possible (e.g., the sheet could include projections that the molded devices 102 are molded around or the surface of the sheet may be porous for example paper). In some embodiments it is desirable for the device 102 to be easily separated from the sheet 104, and in other embodiments it is desirable for the devices to be difficult to separate from the sheet 104. The geometric configuration can be varied depending on the desired type of connection between the devices and the sheet 104. In the depicted embodiment the sheet itself is embossed on the back side. Such embossing can occur as when the mold sides 18, 20 are pressed together during the molding process. In some embodiments the embossing is used to provide an easy way to visually identify the device 102. In an alternative embodiment the carrier web includes a shape that is thermoformed thereon instead of embossed.

Figure 14:
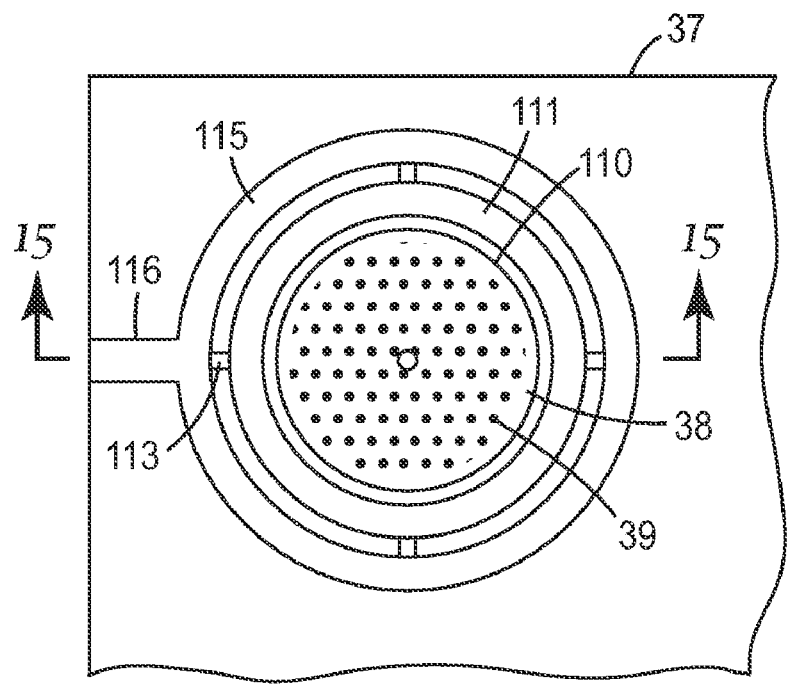
FIG. 14 is a front view of a mold cavity showing parting lines vents and overflows.
Figure 15:
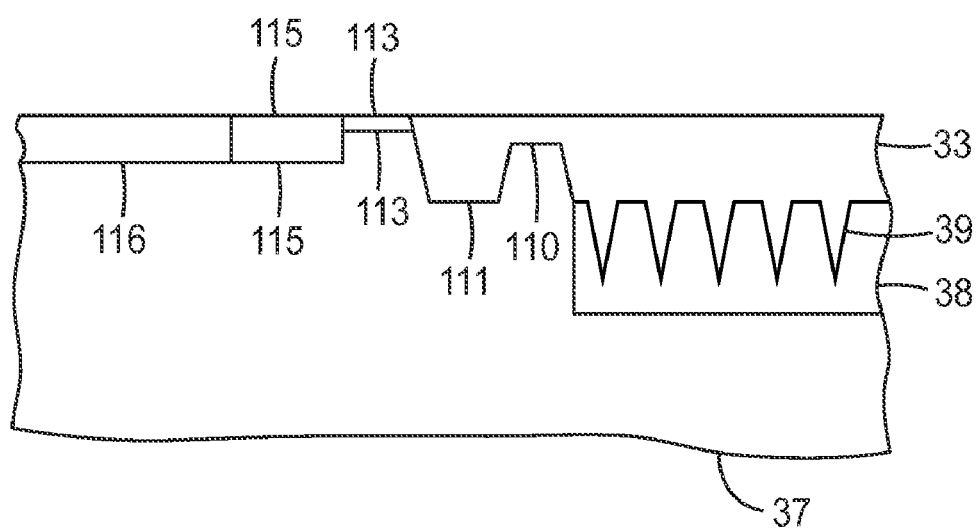
FIG. 15 is a partial sectional view of the mold cavity of FIG. 14.

FIGS. 14 and 15 illustrate a mold cavity that can be used for molding articles with an overflow vent (see WO 2007/075806, page 11) to increase the likelihood of filling all the small features within the cavity. With the use of an overflow vent, the quantity of polymer melt injected into the cavity is greater than the quantity required to fill the cavity. The excess polymer can flow out through a venting means, such as flowing over mold overflow gate 110 into overflow channel 111, from there exiting through primary vent 113, secondary vent ring 115 and vent 116 which vents outside of the mold. The dimensions of these items are within the skill of the art, but example depths would be: overflow gate 381 µm; overflow channel 762 µm; primary vent 127 µm; and secondary vent ring and vent 762 µm.

The inventive process which combines ultrasonics and injection molding on a carrier web can be operated at a shorter mold cycle time than known processes. The cycle time typical of an injection molding process making microneedles using only dynamic mold temperature cycling is 60-80 seconds. Data have shown cycle time for an injection molding process making microneedles using runners between molded articles and ultrasonic vibrations to assist in filling the mold cavity of 14.0 seconds. Data have shown cycle time for the inventive process making microneedles and using a carrier web without runners of 12.0 seconds which is a significant improvement.

Benefits of the inventive process and apparatus include:
1. Indexing of the carrier web enables the process to place a larger number of relatively small molded articles per unit area of the web than would otherwise be feasible (i.e., greater molded part density on the web). This greater utilization of web area may make the process more economical or make it more feasible to use expensive web materials, such as printed circuit web.
2. Mold cycle time reduction discussed above.
3. The ability to mold articles, such as microneedle arrays, having a thinner land portion than could previously be made by injection molding in a very short mold cycle. Thinner microneedle arrays may have an advantage in innoculation or injection applications using certain types of apparatus in which low mass microneedles are desired.
4. The ultrasonic horn must be free to vibrate while the molding machine is closed, and there is a certain clearance (e.g., in the range of 25-50 µm) around the horn (between the horn and surrounding parts in which the horn is mounted or installed) to allow it to vibrate. When the horn or horns are located as shown in FIGS. 2-4, and 7 within the movable mold member, the carrier web between the movable and first mold members can serve as a gasket sealing the mold cavity but allowing the horn to vibrate. The carrier web can prevent molten polymer from leaking into clearance space around the horn and creating mold flash. There is a balance between sufficient clearance around the ultrasonic horn for it to vibrate under the conditions of injection molding and avoiding a space large enough for polymer melt or carrier web to flow into the clearance. That balance can be determined by a person of skill in the art given the information herein, and the dimensions stated in this description are appropriate for that balance.

5. Percent fill at short cycle times is improved over known methods.

6. Percent uniformity (extent to which the microstructural features across an entire array are filled) is improved over known methods. For example, in molding a multiplicity of microneedles in a single mold cavity, the microneedles furthest from the mold cavity gate (where polymer melt enters the cavity) are generally most difficult to make, i.e., for the polymer melt to reach and fill. The inventive method enables filling these microneedles.

7. Injection molding of microneedles or other articles on a web facilitates downstream processing. In an ordinary injection molding process, molded parts ejected from a molding apparatus are dropped into a container from which they may be picked (e.g., by a robot) for later steps. In the inventive method, molded microneedle arrays may be transported on the carrier web to a next step such as coating microneedles. The arrangement of molded articles on the carrier web is advantageous in designing downstream steps.

It was not certain that injection molding on a carrier web could be successfully combined with the application of ultrasonics to improve the molding process. There was some concern that a carrier web would not survive the process conditions of injection molding pressures, temperature changes and the impact of ultrasonic energy. The inventive method and apparatus have overcome this concern.

The following example is illustrative and should not be construed as limiting the invention in any way.

EXAMPLE

An 8 cavity center gated hot runner mold was used to deliver molten polycarbonate resin at 293° C. to a circular mold cavity containing an insert having 1288 microcavities for microneedles 250 µm tall with an aspect ratio of about 3, a pitch (W) of 275 µm and tips having a 5 µm radius, to be molded on a circular land or disc about 1.4 cm in diameter. Experiments were conducted with and without EMI heating using a pneumatically driven linear actuator to place an external 1500 W EMI heater between the first and movable members of the injection mold. Electromagnetic induction was applied for periods ranging from 3 to 8 seconds using a gap of 1 mm between the end of the induction coil housing and the plane of the mold plate face. A hot manifold system was used to feed polymer melt to the mold cavities via the hot runners. A polycarbonate carrier web was indexed between the first and movable mold members.

Vertical movement of the linear actuator for the electromagnetic induction heater was driven by a two-way solenoid valve operating with pressurized air (689 kPa) and was actuated using the robot interface of the 100 ton injection molding machine. The steps of the experiments were:

1. The EMI heater was placed precisely in relationship to the mold cavity, and it was activated.
2. The EMI heater was returned to a home position outside of the space between the first and movable mold members.
3. The mold was closed by moving the movable member toward the first mold member to close the mold with the carrier web between the movable and first members, and polymer melt was injected into the mold cavities.
4. Ultrasonic energy was applied by a cylindrical, axially oriented horn at 20 KHz.
5. The movable mold member moved back from the first mold member, and the molded articles separated from the mold cavity by means of the tension of the carrier web, followed by indexing of the carrier web in preparation for the next plastic shot. The fidelity of the injection molded articles made in the cavity heated by EMI is shown in the table below. Ten replicas were made for each process condition reported.

| Induction Activation Time | Microneedle Height | Percent Uniformity | Percent Fill |
| --- | --- | --- | --- |
| 3 sec. | 230 µm (+/−) 10 µm | 60% | 100% |
| 5 sec. | 240 µm (+/−) 10 µm | 90% | 100% |
| 8 sec. | 250 µm (+/−) 5 µm | 100% | 100% |

It is believed that, because the temperature difference between the polymer melt and the mold cavity surface is reduced (by comparison with known techniques) when EMI is used in the inventive process, the resulting molded article will not experience shrinkage to the same extent as parts molded in conventional processes. Articles made without EMI display an interference pattern when viewed under a 45° cross polarizer indicating anisotropy; whereas, a microneedle array made using EMI as described above showed a distinctly different pattern under polarized light indicating a reduction in anisotropy. With the use of EMI, in-mold stress due to shrinkage is mitigated.

The above specification, examples, and data provide a complete description of the manufacture and use of the inventions. Many additional embodiments of the inventions can be made without departing from the spirit and scope of the inventions. For example, this invention can be carried out using a stack mold configuration.

What is claimed is:

1. A method of injection molding comprising:
   providing an injection molding apparatus having a first mold member and at least one movable mold member that can move toward and away from the first mold member to close the mold, in which there is a mold cavity, in at least one of the first or movable mold members;
   injecting a polymer melt into the mold cavity while it is closed;
   applying ultrasonic vibrations to the mold cavity by means of an ultrasonic horn;
   which method is characterized by:
   positioning a carrier web so that, when the mold is closed, the carrier web is between the first mold member and the moving mold member, part of the web faces the mold cavity and part of it is outside of the closed mold;
   heating the mold cavity by an electromagnetic induction heating means; and
   the mold cavity having a plurality of microstructural features having an aspect ratio of at least 2:1 or the mold cavities in both the first and movable mold members between which the carrier web is positioned.

2. The method of claim 1 in which, for one molding cycle, a first portion of the carrier web is positioned facing the mold cavity and a second portion of the carrier web up-web of the first portion is not facing the mold cavity; and the method further comprises indexing the carrier web to a next position in which the first portion is down-web of the mold cavity and the second portion is facing the mold cavity for the next molding cycle.

3. The method of claim 1 in which the melt is injected into the mold cavity from a first side of the mold cavity and the ultrasonic vibrations are applied from a second side of the mold cavity.

4. The method of claim 3 in which the ultrasonic vibrations are applied to the carrier web facing the mold cavity.

5. The method of claim 1 which further comprises removing a molded article from the mold cavity by means of the carrier web without the use of mechanical ejector means including ejector pins, lifters or a stripper plate.

6. The method of claim 1 in which the mold cavity is configured to mold microneedles.

7. The method of claim 1 in which the carrier web comprises a material selected from polymer film, metal foil, woven or nonwoven cloth, paper and a composite web of metal and polymer, cloth and polymer or paper and polymer.

8. The method of claim 1 in which the carrier web has features including undercuts or projections that interlock with the article to be molded.

9. The method of claim 1 in which the carrier web has holes, perforations, slits, grooves and/or surface texture effective to provide venting during injection molding.

10. The method of claim 1 in which the injection gate is at the center of one side of the mold cavity.

11. The method of claim 1 in which there are mold cavities in both the first and movable mold members and mold features in both mold cavities and one of the two mold cavities has features of a lower aspect ratio than the features of the other mold cavity.

12. The method of claim 11 in which the features of the two mold cavities are opposite to each other so that they form a lens or lenses in the resulting molded article.

13. An injection molding apparatus comprising:
a first mold member;
a moving mold member that can move toward and away from the first mold member;
a mold cavity within the first mold member and facing the moving mold member;
a web handling means for moving a carrier web between the first mold member and the moving mold member so that part of the carrier web faces the mold cavity and part of the carrier web is outside of the area enclosed by the first and moving mold members when they are in the closed position;
a means to inject melt into the mold cavity; and
an ultrasonic system for providing ultrasonic vibrations to the melt in the mold cavity;
characterized by further comprising:
A. a web indexing means to index the carrier web to a different position along its length each time the moving mold member moves toward the first mold member to close the mold; and
B. an electromagnetic induction heater capable of heating a mold insert within the mold cavity and/or metal surrounding the mold cavity.

14. The apparatus of claim 13 in which the ultrasonic system includes a resonant horn, an ultrasonic converter, and a booster.

15. The apparatus of claim 13 further comprising a metal insert within the mold cavity and in which the insert is used as an electrical resistance heater.

16. The apparatus of claim 13 in which the first mold member has an offset or recess that allows injection molding to occur while articles already molded on the carrier web are within the perimeter of the first and movable mold members when they are in the closed position, leaving such articles undamaged.

17. The apparatus of claim 16 in which the movable mold member also has an offset or recess allowing injection molding to occur on the side of the carrier web facing the movable mold member while articles already molded on that side of the carrier web are within the perimeter of the first and movable mold members when they are in the closed position, leaving such articles undamaged.

* * * * *